US006235277B1

(12) United States Patent
Jean

(10) Patent No.: US 6,235,277 B1
(45) Date of Patent: May 22, 2001

(54) DEODORANT GRANULATES FOR ASHTRAYS

(76) Inventor: Marcel Jean, 168 Chemin du Chateau, 06250 Mougins (FR)

( * ) Notice: Subject to any disclaimer, the term of this patent is extended or adjusted under 35 U.S.C. 154(b) by 0 days.

(21) Appl. No.: 09/029,741

(22) PCT Filed: Sep. 12, 1996

(86) PCT No.: PCT/FR96/01405

§ 371 Date: May 13, 1998

§ 102(e) Date: May 13, 1998

(87) PCT Pub. No.: WO97/10009

PCT Pub. Date: Mar. 20, 1997

(30) Foreign Application Priority Data

Sep. 13, 1995 (FR) .................................. 95 10987

(51) Int. Cl.[7] .............. A61L 9/01; A61K 31/74
(52) U.S. Cl. ........ 424/76.1; 424/76.2; 424/76.3; 424/76.4; 424/76.8; 424/78.03; 424/78.31; 424/401
(58) Field of Search ............... 424/76.1, 78.03, 424/78.31, 76.2, 76.3, 76.4, 76.8, 401

(56) References Cited

U.S. PATENT DOCUMENTS 4,395,357 * 7/1983 Kramer et al. ...................... 252/428
5,145,673 * 9/1992 Koizumi .............................. 424/76.1
5,159,941 * 11/1992 Tornatore ............................ 131/236
5,165,915 * 11/1992 Tokubo et al. ......................... 424/63
5,182,103 * 1/1993 Nakane et al. .................... 424/78.03
5,539,034 * 7/1996 Caupin et al. ....................... 524/315
5,738,118 * 4/1998 Ikoma ................................ 131/328

FOREIGN PATENT DOCUMENTS 0250304 12/1987 (EP) .
2024014 1/1980 (GB) .
2217603 11/1989 (GB) .

* cited by examiner

Primary Examiner—Jose' G. Dees
Assistant Examiner—Kathryne E. Shelborne
(74) Attorney, Agent, or Firm—Greenblum & Bernstein, P.L.C.

(57) ABSTRACT

Deodorant granulate for lining ashtrays for receiving tobacco ash, including an active component. The active component includes perfume which is one of aromatic and suitable for use on the human body, high viscosity solvent with low evaporation, and undecylenic acid deodorant. The active component is incorporated into non-inflammable mineral granulates whose granularity is selected so as not to leave any trace of dust when used, and has a porosity that enables the mineral granulate to absorb at least 15 wt % of the active component, and to release the active component upon contact with a lit cigarette or cigar. Method for lining ashtrays.

20 Claims, No Drawings

DEODORANT GRANULATES FOR ASHTRAYS

This application is a 371 of PCT/FR96/01405 filed Sep. 12, 1996.

BACKGROUND OF THE INVENTION

1. Field of the Invention

The present invention relates to deodorant granulates for ashtrays.

They are adapted to line the base of all types of ashtrays receiving tobacco ash. Indeed, they can be used in table ashtrays as well, whether in homes, bars or restaurants, and in large capacity ashtrays located in public areas such as train stations, airports, or large commercial areas, and also in car ashtrays.

2. Discussion of Background

It is well-known that tobacco odors, especially those emanating from ashtrays, are among the most undesirable. One of the most unpleasant odors is that of cold tobacco.

The rapid development over the last few years of anti-smoking campaigns has given rise to increasingly more restrictive legislation, especially as regards non-smoking areas in restaurants and public areas.

The solutions found up until now to suppress the perception of tobacco odors coming from ashtrays have a very limited scope, and in order to obtain appreciable results, they have had to be associated with masking techniques so as to cover the tobacco odor, qualified as unpleasant, by another odor, perceived as pleasant.

As a result, in most cases, deodorizing performances are unequal to the task, since the perfumes that are used are generally perceived as being too strong, which affects the pleasure of the individual smoking, without really satisfying the non-smoker who has often imposed the use of "anti-tobacco" products on the smoker. This is especially true in the case of anti-tobacco deodorants for ashtrays.

It is obvious that a product which could suppress tobacco odors coming from the ashtray, its diffusion being accelerated from the time one starts smoking and that is capable of filling the air with a pleasant odor for everybody in the immediate area, whether it be a restaurant, office, lounge, etc., could restore a "natural" conviviality between smokers and non-smokers.

Today, carriers for anti-tobacco products for ashtrays are:
  either fine non-porous sand, colored and scented by coating, or porous but with little receiving capacity for the active product, because of its fineness;
  or larger-sized granulates of various materials, for example, of plastic material.

Their active product either promotes the deodorizing performance or the covering of the odor by very strong perfumes, but no product effectively associates the three elements that are necessary for a good final result:
  a deodorizing system significantly reducing the unpleasant perception of tobacco odor and especially that of cold tobacco;
  a high quality perfume that is sufficiently volatile so as to be diffused almost instantly as soon as it is touched by the incandescent end of the cigarette;
  a non-inflammable carrier capable of receiving, retaining and releasing the active products at the right time, i.e., as soon as it comes into contact with the incandescent end of the cigarette.

SUMMARY OF THE INVENTION

The product according to the instant invention relates to improving this situation. Indeed, it allows, at a very reasonable cost, the complete neutralizing of tobacco odors from the ashtray, while delicately perfuming the atmosphere, and this is done without detracting from the pleasure of the smoker, thereby providing the maximum in olfactory comfort.

The deodorant for ashtrays is formed of an active component containing a perfume of aromatic type or suitable for use on the human body, a weakly volatile solvent and an undecylenic acid deodorant, said active component being incorporated into granulates formed from a non-inflammable mineral carrier of a selected granularity so as not to leave any trace of dust when used, and of a porosity that enables it to receive a substantial amount of the active product and to release it upon contact with a lit cigarette.

DETAILED DESCRIPTION

The following detailed description relates to a non-limiting example of one of the embodiments of the object of the invention.

The product targeted by the invention takes the form of granulates that combine a carrier having a high melting point and a well-defined granulometry, a high quality perfume, a high viscosity solvent with low evaporation, and a deodorizing ingredient.

The carrier is a defining element for the effectiveness of the ease of use of the product. It must have the highest possible melting point, and pumice stone or washing stone, which has a melting point of 1500° C., is perfect in this regard.

Its granulometry must be perfectly defined: if it is too fine, it will either produce unwanted dust for the user, or it will not correctly receive substantial proportions of the active compound; if it is too coarse, it will fulfill its function poorly. A good size for the smallest granulates is 2–3 mm, and 5–8 mm for the largest. Granulates that are lightly polished into pebbles will be used advantageously.

This is a common product in this industry, wherein it has numerous applications as an abrasive; its cost is very inexpensive. Finally, its porosity (density of about 0.6 g/cm$^3$) allows it to receive 15–20% of the active compound necessary for obtaining optimum effectiveness by merely spreading a thin layer at the bottom of the ashtray. The impregnation period is very short, and the granulates become perfectly dry in a few minutes, thus the smell will not be transferred to the cigarette placed in the ashtray, even a non-lit cigarette.

The perfume used is the type used for body perfumes, and conforms to the requirements recognized by professionals in the perfume industry, and especially to the French standard IFRA [International Fragrance Association] and the recommendations of the US agency RIFM [Research Institute for Fragrance Material].

This type of perfume must be sufficiently volatile so that the olfactory comfort of perfuming the atmosphere is comparable, on all fronts, to that of body perfuming. It will advantageously contain hesperidins (especially lemon) which have always proven their deodorizing abilities.

It could also agreeably restore alimentary or gourmet smells with the same olfactory comfort.

The solvent will preferably be monopropylene glycol, but can also consist of polypropylene glycol or a compound with similar characteristics.

Propylene glycol is largely recognized as being one of the best carriers of quality perfumes, capable of agglomerating possible traces of dust through its viscosity, and of controlling the output of the perfume incorporated into the porous carrier through its low evaporation. It consists of a solvent having a melting point that is high enough to provide a reduced inflammability to the aromatic materials by sufficiently lowering the flash point of the active product so as to cause the automatic extinguishing of the small flames which could ignite, for example, in the case of lit matches that are left in the ashtray.

The deodorizing ingredient selected is undecylenic acid (known as "C11"), obtained from ricin oil, and which has proven its effectiveness when the dose is perfectly controlled.

In this case, it is used as ethyl undecylenate which is an ester of undecylenic acid and ethanol, whose cosmetic quality is well known. An appropriate dose allows its own odor to be used as one of the constitutive elements of the perfume, as was demonstrated by our own experiments.

To make the active product, the perfume and the solvent will be advantageously combined in proportions comprising between 20/80 and 50/50, and for the deodorizing ingredient, the most conclusive results were obtained by incorporating substantially 3% of ethyl undecylenate.

This active product will then take up 15-20% in weight of the mineral carrier retained for this application.

The granulates can be easily colored by incorporating colorings, that have been approved in perfumeries, directly into the active product, in proportion of about 3% solution, containing 2-4% coloring, into water or monopropylene glycol.

For an advertising or marketing objective, the deodorizing function can actually be visualized by coloring a small part of the granulates differently. Therefore, by way of example, a small quantity of green grains in a product of a different color could symbolize the presence of a deodorant of natural origin.

The granulates for ashtrays thus obtained by assembling an active product constituted of perfume, monopropylene glycol, ethyl undecylenate and coloring incorporated into pumice stone granulates, provide maximum effectiveness and results unknown to this day, appreciated by smokers and non-smokers alike.

When placed in automobile ashtrays for non-smokers, they will maintain a fresh and unobtrusive atmosphere for a long time, the output being adjustable by the opened width of the ashtray.

The smoker has a product that does not detract from his pleasure. Indeed, the volatile nature of specially formulated perfumes means that they evaporate as soon as they come into contact with the incandescent end of the cigarette or cigar. Thus, there is no ill-timed perfuming of the tobacco smell, and the smoker's pleasure remains intact.

An appropriate dose of the undecylenic acid makes the deodorizing effect almost complete, which can be noticed both by smelling the evaporated smoke from the ashtray which has no unpleasant tobacco odor, as well by smelling the ashtray emptied after use, where practically no residual odor is smelled, especially practically no extremely unpleasant odor of cold tobacco.

The perfuming effect is immediate and intervenes at the right time. The granulates in the ashtray act relatively weakly when at rest, but as soon as there is contact with the incandescent end of the cigarette, the perfume from the granulates is quickly evaporated and carried away by the smoke into the atmosphere with the undecylenic acid. There are no more unpleasant tobacco odors generated from the ashtray.

Since the perfuming effect reaches its optimum level by the quality of the perfume that evaporates, the atmosphere remains virtually unpolluted by the smoke exhaled by the smoker. This is the non-smoker's primary wish. One can go as far as claiming that the effect obtained is likely to reinstate cohabitation between smokers and non-smokers.

The positioning of the various constitutive elements gives the object of the invention a maximum of useful effects which had not been obtained by similar products to this day.

What is claimed is:

1. Deodorant granulate for lining ashtrays for receiving tobacco ash, the deodorant granulate comprising:
   an active component comprising:
      perfume which is one of aromatic and suitable for use on the human body,
      high viscosity solvent with low evaporation, and
      undecylenic acid deodorant;
   the active component being incorporated into non-inflammable mineral granulates whose granularity is selected so as not to leave any trace of dust when used, and having a porosity that enables the mineral granulate to absorb at least 15 wt % of the active component, and to release the active component upon contact with a lit cigarette or cigar.

2. Deodorant granulate of claim 1, wherein the high viscosity solvent comprises monopropylene glycol.

3. Deodorant granulate of claim 1, wherein the mineral granulate has a density of about 0.6 g/cm$^3$ and comprises one of pumice stone and washing stone.

4. Deodorant granulate of claim 1, wherein the mineral granulate comprises pebbles having a size range of 2 to 8 mm.

5. Deodorant granulate of claim 1, wherein the mineral granulate comprises lightly polished pebbles having a size range of 3 to 5 mm.

6. Deodorant granulate of claim 1, wherein the perfume is suitable for use on the human body.

7. Deodorant granulate of claim 6, wherein the perfume is made only from materials conforming to requirements of International Fragrance Association and Research Institute for Fragrance Material.

8. Deodorant granulate of claim 1, wherein the perfume comprises an aromatic perfume.

9. Deodorant granulate of claim 8, wherein the aromatic perfume has alimentary odor.

10. Deodorant granulate of claim 1, wherein the perfume and the high viscosity solvent are combined in proportions comprising between 20 parts perfume for 80 parts solvent, and 50 parts perfume for 50 parts solvent.

11. Deodorant granulate of claim 1, wherein the active component substantially contains 3% of ethyl undecylenate.

12. Deodorant granulate of claim 1, wherein the deodorant granulate comprises 15-20% of the active component.

13. Deodorant granulate of claim 1, wherein the deodorant granulate is colored by incorporation into the active component of colorants approved in perfumeries, in proportion of about 3% solution containing 2-4% coloring, into one of water and monopropylene glycol.

14. A method of lining ashtrays, comprising:

lining an ashtray with a deodorant granulate, the deodorant granulate comprising an active component incorporated into non-inflammable mineral granulates;

the active component comprising:
perfume which is one of aromatic and suitable for use on the human body,
high viscosity solvent with low evaporation, and
undecylenic acid deodorant;

the non-inflammable mineral granulates incorporating the active component having granularity selected so as not to leave any trace of dust when used, and having a porosity that enables the mineral granulate to absorb at least 15 wt % of the active component, and to release the active component upon contact with a lit cigarette or cigar.

15. The method of claim 14, wherein the ashtray comprises a table ashtray used in one of a home, a bar, and a restaurant.

16. The method of claim 14, wherein the ashtray comprises a large capacity ashtray.

17. The method of claim 16, wherein the large capacity ashtray is located in a public area.

18. The method of claim 17, wherein the public area is one of a train station, an airport, and a large commercial area.

19. The method of claim 14, wherein the ashtray comprises a car ashtray.

20. The method of claim 14, wherein the mineral granulate comprises pebbles having a size range of 2 to 8 mm.

\* \* \* \* \*